United States Patent [19]

Kelley

[11] 4,404,198
[45] Sep. 13, 1983

[54] PHENYL SALICYLATE AS A TOPICAL ANTI-INFLAMMATORY

[75] Inventor: Kane L. Kelley, Roselle, N.J.

[73] Assignee: Beecham Inc., Clifton, N.J.

[21] Appl. No.: 233,767

[22] Filed: Feb. 12, 1981

Related U.S. Application Data

[63] Continuation-in-part of Ser. No. 142,873, Apr. 23, 1980, abandoned, which is a continuation of Ser. No. 5,963, Jan. 24, 1979, abandoned.

[51] Int. Cl.³ .................... A61K 31/605; A61K 31/60
[52] U.S. Cl. ...................................... 424/235; 424/230
[58] Field of Search ........................ 424/230, 231, 235

[56] References Cited

U.S. PATENT DOCUMENTS

| | | | |
|---|---|---|---|
| 1,471,344 | 10/1923 | Loudin | 424/230 |
| 3,091,511 | 5/1963 | Calhoun | 424/230 |
| 3,657,430 | 4/1972 | Shen et al. | 424/230 |
| 3,657,431 | 4/1972 | Shen et al. | 424/230 |
| 4,003,999 | 1/1977 | Lybrand et al. | 424/230 |
| 4,136,165 | 1/1979 | Möller et al. | 424/230 |

OTHER PUBLICATIONS

The Merck Index, 9th ed. (1976)–Merck & Co. Inc. item 7116.
Chem. Abst. 38, 6490 (1) (1944)–Termansen.

*Primary Examiner*—Douglas W. Robinson
*Attorney, Agent, or Firm*—Jacobs & Jacobs

[57] ABSTRACT

Phenyl salicylate has been found to be useful as a topical anti-inflammatory. It is particularly effective when combined with eugenol for the treatment of UV-induced erythema.

16 Claims, No Drawings

PHENYL SALICYLATE AS A TOPICAL ANTI-INFLAMMATORY

This is a continuation-in-part of my co-pending application Ser. No. 142,873 filed Apr. 23, 1980 now abandoned which is itself a continuation of my application Ser. No. 005,963 filed Jan. 24, 1979, now abandoned.

Phenyl salicylate is known in the art as an analgesic, antipyretic and antirheumatic. It is also known to be used as an intestinal antiseptic, for the treatment of diarrhea, as an external disinfectant and for sunburn prevention. In addition, phenyl salicylate has been used as an enteric coating for tablets.

Eugenol is known in the art as a dental analgesic and in the perfumery art it is used instead of oil of cloves and in the manufacture of vanillin.

The instant invention is based on the surprising discovery that phenyl salicylate is useful as a topical anti-inflammatory and may be combined with a suitable pharmaceutically acceptable carrier into a topical application form composition and applied to the skin of a human or animal which is inflamed.

According to one embodiment of the invention, the concentration of phenyl salicylate in the topical composition is from about 0.1% to about 10.0%.

According to a further embodiment of the present invention, the concentration of phenyl salicylate is from about 1.0% to about 10.0%, preferably from about 1.0% to about 5.0%. According to a further embodiment of the present invention, the concentration of phenyl salicylate is from about 0.1% to about 2.5%, preferably about 1.0%. According to a further embodiment of the present invention, the concentration of phenyl salicylate is from about 3.0% to about 5.0%.

According to another embodiment of the present invention, the pharmaceutically acceptable carrier with which phenyl salicylate is combined is a lower alcohol. Ethyl alcohol is especially preferred.

According to another embodiment of the present invention, the carrier is benzyl alcohol or propylene glycol.

According to another embodiment of the present invention, the carrier is a mixture of one or more lower alkanols in combination with propylene glycol.

According to another embodiment of the present invention, the carrier is one or more lower alkanols in combination with propylene glycol and benzyl alcohol.

According to a preferred embodiment of the present invention, the concentration of phenyl salicylate is about 1% and the carrier is a lower alkanol or propylene glycol.

Although the phenyl salicylate may be advantageously applied topically to the skin per se, an enhancement of the anti-inflammatory activity occurs when eugenol is incorporated into the formulation. The inclusion into the formulation of nontoxic solvents, surfactants, emollients, oils, etc., which are compatible with phenyl salicylate may be employed.

In addition, one may combine topical anesthetics and analgesics with this formulation.

It has also been discovered that the use of phenyl salicylate for the treatment of UV-induced erythema is enhanced by the addition of eugenol.

According to that embodiment of the present invention, the amount of phenyl salicylate should be from about 1.0% to 10.0% and the amount of eugenol should be from about 0.1% to 2.0%. The carriers may be any of the above referred to carriers and the resultant pharmaceutical composition is as described above in topical application form so that it may be applied to the skin of a human or animal suffering from inflammation.

It has been found to be advantageous to include in the compositions of the present invention a penetrating agent such as methyl salicylate. The presence of such an agent in the amount of 1% to 10%, preferably 2% to 5% and particularly about 3%., substantially enhances the ability of the present compositions to penetrate the skin, thereby enhancing effectiveness.

The concentration of phenyl salicylate is not critical and will depend, as one skilled in the art will appreciate, upon a variety of factors including, location, type and severity of the disorder being treated.

The amount applied topically will vary, depending upon a number of considerations. In this regard, the art further appreciates that in many instances a relatively strong concentration or more frequent application of a weaker concentration may be equally effective. The objective is to obtain the maximum therapeutic response with minimum dosage.

The following non-limitative examples more particularly illustrate the present invention:

EXAMPLE 1

The following ingredients are combined to form a topical composition:
5% Phenyl Salicylate and 0.25% eugenol in a vehicle consisting of:
 3% Methyl Salicylate
 12% Propylene Glycol
 85% Absolute Ethyl Alcohol.

EXAMPLE 2

The following ingredients are combined to form a topical composition:
2.5% Phenyl Salicylate and 0.5% eugenol in a vehicle consisting of:
 20% Propylene Glycol
 80% Absolute Ethyl Alcohol.

EXAMPLE 3

The following ingredients are combined to form a topical composition:
1% Phenyl Salicylate and 1% Eugenol in a vehicle consisting of:
 3% Methyl Salicylate
 5% Benzyl Alcohol
 12% Propylene Glycol
 40% Isopropyl Alcohol
 40% Absolute Ethyl Alcohol.

EXAMPLE 4

The following ingredients are combined to form a topical composition:
10% Phenyl Salicylate and 0.1% Eugenol in a vehical consisting of:
 0.25% Oil of Allspice
 0.25% Oil of Bay
 3.0% Methyl Salicylate
 5.0% Benzyl Alcohol
 15.0% Propylene Glycol
 76.5% Absolute Ethyl Alcohol.

EXAMPLE 5

The following ingredients are combined to form a topical composition:

1% Phenyl Salicylate in a vehicle consisting of
3% Methyl Salicylate
5% Benzyl Alcohol
12% Propylene Glycol
40% Isopropyl Alcohol
40% Absolute Ethyl Alcohol.

EXAMPLE 6

The following ingredients are combined to form a topical composition:
2.5%–3.0% Phenyl Salicylate in vehicle consisting of
20% Propylene Glycol
80% Absolute Ethyl Alcohol.

EXAMPLE 7

The following ingredients are combined to form a topical composition:
5% Phenyl Salicylate in a vehicle consisting of
3% Methyl Salicylate
12% Propylene Glycol
85% Absolute Ethyl Alcohol.

EXAMPLE 8

A topical composition was prepared by combining the following ingredients:
5% Phenyl Salicylate in absolute ethanol q.s.

EXAMPLE 9

A topical composition was prepared by combining the following ingredients:
10% Phenyl Salicylate in a vehicle consisting of
0.25% Oil of Allspice
0.25% Oil of Bay
3.0% Methyl Salicylate
5.0% Benzyl Alcohol
15.0% Propylene Glycol
76.5% Absolute Ethyl Alcohol.

What is claimed is:

1. A method of treating inflammation in humans and animals which comprises topically applying to the inflamed area an anti-inflammatory amount of a composition which comprises from about 0.1% to about 10.0% of phenyl salicylate in combination with a pharmaceutically acceptable carrier suitable for topical application to the skin of a human or animal.

2. A method according to claim 1 wherein the concentration of phenyl salicylate is from about 1.0% to about 10.0%.

3. A method according to claim 1 wherein the concentration of phenyl salicylate is from about 1.0% to about 5.0%.

4. A method according to claim 1 wherein the concentration of phenyl salicylate is from about 0.1% to about 2.5%.

5. A method according to claim 1 wherein the concentration of phenyl salicylate is from about 3.0% to about 5.0%.

6. A method according to claim 1 wherein the concentration of phenyl salicylate is about 1%.

7. A method according to claim 1 wherein the carrier is a lower alkanol.

8. A method according to claim 7 wherein the lower alkanol is ethanol.

9. A method according to claim 1 wherein the carrier is benzyl alcohol.

10. A method according to claim 1 wherein the carrier is propylene glycol.

11. A method according to claim 1 wherein the concentration of phenyl salicylate is about 1.0% and the carrier is a mixture of benzyl alcohol, propylene glycol, isopropyl alcohol and absolute ethyl alcohol.

12. A method according to claim 1 wherein the concentration of phenyl salicylate is about 2.5% to 3.0% and the carrier is a mixture of propylene glycol and absolute ethyl alcohol.

13. A method according to claim 1 wherein the concentration of phenyl salicylate is about 5.0% and the carrier is a mixture of propylene glycol and absolute ethyl alcohol.

14. A method according to claim 1 wherein the concentration of phenyl salicylate is about 5.0% and the carrier is absolute ethyl alcohol.

15. A method according to claim 1 wherein the concentration of phenyl salicylate is about 10.0% and the carrier is a mixture of benzyl alcohol, propylene glycol and absolute ethyl alcohol.

16. A method according to claim 1 wherein the concentration of phenyl salicylate is about 1% and the carrier is a lower alkanol or propylene glycol.

* * * * *